United States Patent
Al-Sebeih

(10) Patent No.: US 11,083,569 B1
(45) Date of Patent: Aug. 10, 2021

(54) SEMISOLID GRAFT APPLICATOR

(71) Applicant: Khalid Al-Sebeih, Safat (KW)

(72) Inventor: Khalid Al-Sebeih, Safat (KW)

( * ) Notice: Subject to any disclaimer, the term of this patent is extended or adjusted under 35 U.S.C. 154(b) by 0 days.

(21) Appl. No.: 16/876,014

(22) Filed: May 16, 2020

(51) Int. Cl.
*A61F 2/18* (2006.01)
*A61B 17/34* (2006.01)

(52) U.S. Cl.
CPC .......... *A61F 2/186* (2013.01); *A61B 17/3468* (2013.01); *A61F 2250/0097* (2013.01)

(58) Field of Classification Search
CPC .......... A61F 2/186; A61F 2/148; A61F 2/167; A61F 2002/0072; A61F 2/966; A61F 2/18; A61F 2002/183
See application file for complete search history.

(56) References Cited

U.S. PATENT DOCUMENTS

| | | | |
|---|---|---|---|
| 2003/0236573 A1* | 12/2003 | Evans | A61L 31/042 623/23.58 |
| 2005/0004580 A1* | 1/2005 | Jokiniemi | A61B 90/11 606/130 |
| 2011/0183287 A1 | 7/2011 | Lee | |
| 2014/0243975 A1* | 8/2014 | Saidi | A61B 17/3468 623/10 |
| 2014/0288643 A1 | 9/2014 | Torres et al. | |
| 2016/0331429 A1 | 11/2016 | Jenson | |
| 2019/0117403 A1 | 4/2019 | Schmieding et al. | |
| 2019/0223931 A1 | 7/2019 | Neiber | |
| 2019/0224024 A1 | 7/2019 | Kleiner et al. | |

* cited by examiner

*Primary Examiner* — Wade Miles
(74) *Attorney, Agent, or Firm* — Nath, Goldberg & Meyer; Richard C. Litman

(57) ABSTRACT

A semisolid graft applicator may be used for dispensing a graft during rhinoplasty procedures. The applicator includes a graft container and a pusher. The graft container defines a trough for containing a semisolid graft, such as a graft made from diced cartilage and platelet rich fibrin. A portion of the pusher resides within a tubular sheath of the graft container to guide axial movement between the pusher and graft container. A distal end of the pusher includes a block which slides along the length of the trough when the graft container is moved relative to the pusher.

1 Claim, 3 Drawing Sheets

SEMISOLID GRAFT APPLICATOR

FIELD OF THE INVENTION

The disclosure of the present patent application relates to rhinoplasty graft applicators and, more particularly, to a graft applicator for dispensing a semisolid graft while maintaining the shape and thickness of the graft.

DESCRIPTION OF THE RELATED ART

Rhinoplasty is considered to be one of the most common and difficult plastic surgery operations. Adjustment of the dorsum of the nose is one of the main steps in a rhinoplasty operation. In some cases, the dorsum has to be reduced, while in other cases the dorsum has to be augmented. Augmentation of the dorsum of the nose can be achieved by different techniques using cartilage grafts or alloplastic materials. The grafts can be harvested from the septal cartilage, auricular cartilage, or costal cartilage.

Applying the cartilage to the dorsum of the nose can be done by various techniques. In one technique, the cartilage can be carved and fixed to the dorsum as a solid piece. However, when this technique is used, the cartilage edges under the skin can be noticeable. One technique for avoiding this result involves the use of diced cartilage. However, diced cartilage alone is very loose and will not give the bulk and the support required for augmentation. To gain the required support and strength for the diced cartilage graft, the diced cartilage can be mixed with platelet-rich fibrin (PRF).

PRF is an autologous concentrated blood derivative that can be prepared from the patient's own blood. PRF contains growth factors that accelerate tissue healing and reduce the resorption rate of the diced cartilage in the nasal dorsum. When the diced cartilage is mixed with the PRF (DCPRF), a semisolid piece of diced cartilage can be manipulated and shaped to augment the dorsum of the nose.

One problem with grafting the DCPRF is applying it to the dorsum of the nose. Holding DCPRF with forceps can be destroy and disperse the DCPRF. Conventional instruments fail to efficiently apply the DCPRF to the dorsum of the nose in the specific desired position without disturbing the shape and the thickness of the graft.

Thus, a semisolid graft applicator solving the aforementioned problems is desired.

SUMMARY OF THE INVENTION

The semisolid graft applicator, which may be used for rhinoplasty procedures, includes a graft container and a pusher. The graft container defines a trough for containing a semisolid graft, such as a graft made from diced cartilage and platelet rich fibrin. A portion of the pusher resides within a tubular sheath of the graft container to guide axial movement between the pusher and graft container. A distal end of the pusher includes a block which slides along the length of the trough when the graft container is moved relative to the pusher.

During a rhinoplasty procedure, the graft container is loaded with a graft and inserted into the tissue of a patient's nose. When the practitioner determines the graft is at an appropriate position, the graft container is then pulled out of the nose while the pusher remains in place to hold the graft at the set position. As a result, the graft is implanted in the desired location while maintaining its size and shape.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The present subject matter is directed to a semisolid graft applicator which may be used for rhinoplasty procedures. The applicator includes a graft container and a pusher slidably received within the graft container. The graft container may include a trough for retaining a semisolid graft, such as a graft made from diced cartilage and platelet rich fibrin. A distal end of the pusher may include a block for disposing the graft in the desired position.

During a rhinoplasty procedure, the applicator can be loaded with a graft and inserted into the nose of a patient. At an appropriate position, the graft container can be pulled out of the nose while the pusher remains in place to hold the graft at the set position. As a result, the graft can be implanted in the desired location while maintaining its size and shape.

Figure 1:
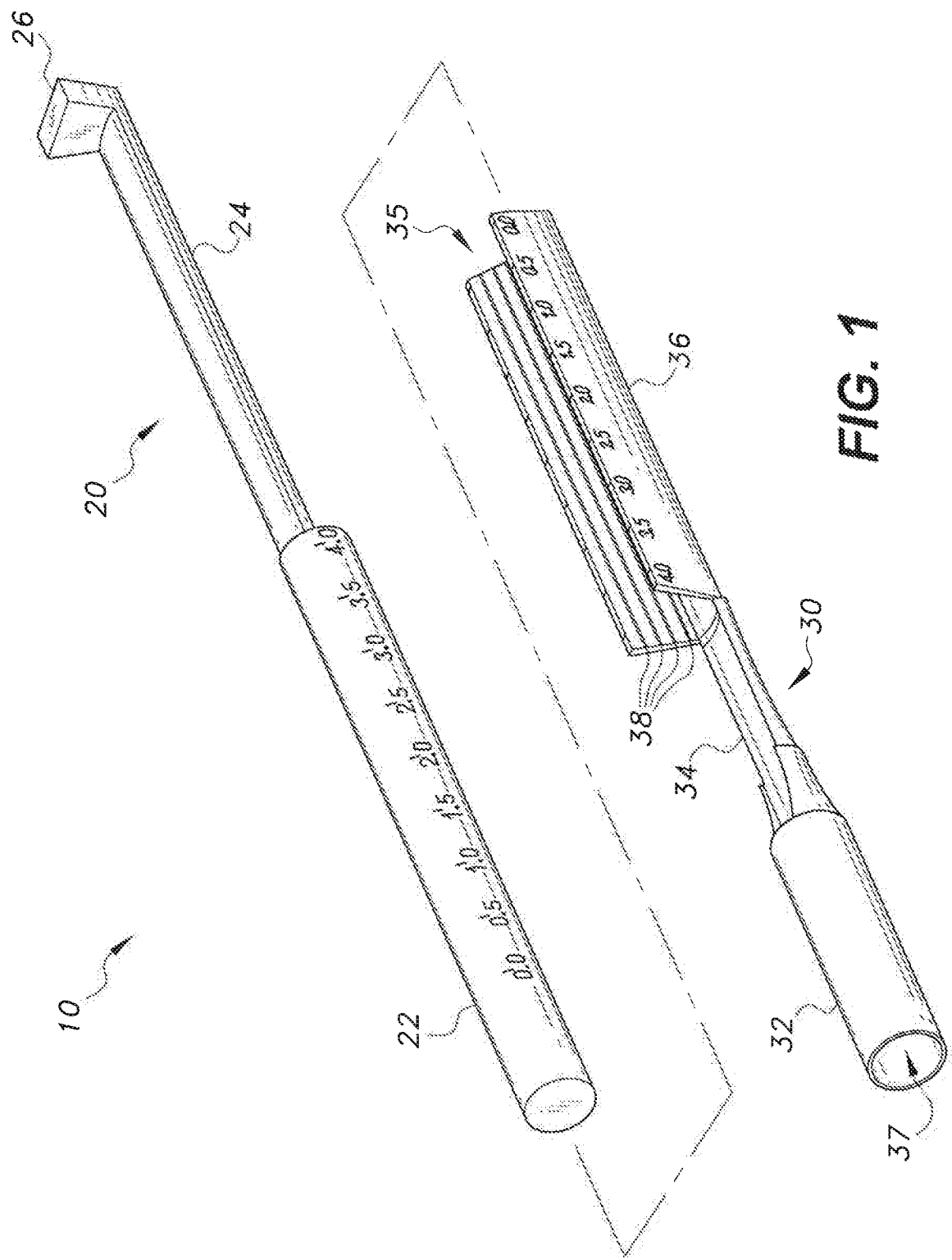
FIG. 1 is an exploded, perspective view of a semisolid graft applicator.

FIG. 1 shows an embodiment of the semisolid graft applicator 10 which includes a graft container 30 and a pusher 20. The graft container 30 may define a distal trough 36, a central guide rail 34, and a proximal sheath 32. The trough 36 may be generally U-shaped to define a channel 35 for accepting and containing a semisolid graft. An outer surface of the trough 36 may include a measuring scale for assisting a practitioner with sizing a graft. The measuring scale may include evenly spaced increments and indicia for indicating a distance between each increment and the distal end of the trough, thereby allowing a user to measure a length of the graft disposed therein. In some embodiments, the measuring scale may include 0 cm to 4 cm, as this range incorporates the size of most grafts applied to the dorsum of the nose. An inner surface of the trough may include thickness lines 38 extending across its length at evenly spaced increments. The thickness lines 38 may be used by a practitioner to assist in preparing a graft having the proper thickness. The guide rail 34 provides a surface for supporting the pusher 20. The guide rail 34 may seamlessly transition into the trough channel 35 to provide for smooth operation between the pusher and graft container. The sheath 32 may be a tubular structure with an inner conduit 37.

The pusher 20 may include a distal block 26, a central elongate portion 24, and a proximal guide member 22. The block 26 may be configured to fit within the channel 35 of the trough 36. Accordingly, when the trough is moved towards the pusher, the block 26 can push all of the semisolid material out of the trough 36 and into the targeted location. The guide member 22 can be cylindrical and configured to fit within the conduit 37 of the sheath 32. The interaction between the guide member 22 and the sheath 32 restricts movement of the pusher to a single axis parallel to the length of the graft container 30.

The block 26 can reach a distal end of the trough 36 while the guide member 22 remains within the sheath 32. A measuring scale may be provided on the outer surface of the guide member 22 to assist a practitioner with sizing and/or deploying the graft. The measuring scale may be configured to indicate the distance between the distal surface of the block and the distal end of the trough based on the point on the scale that is aligned with the proximal end of the sheath 32. The measuring scale may include evenly spaced increments and indicia indicating a length of each increment. The measuring scale on the guide member 22 may be used when the applicator is inserted into a patient's nose and a view of the measuring scale on the trough 36 is blocked. In some embodiments, the central elongate portion 24 may be removably connected to the guide member 22 for assembly purposes.

Figure 2:
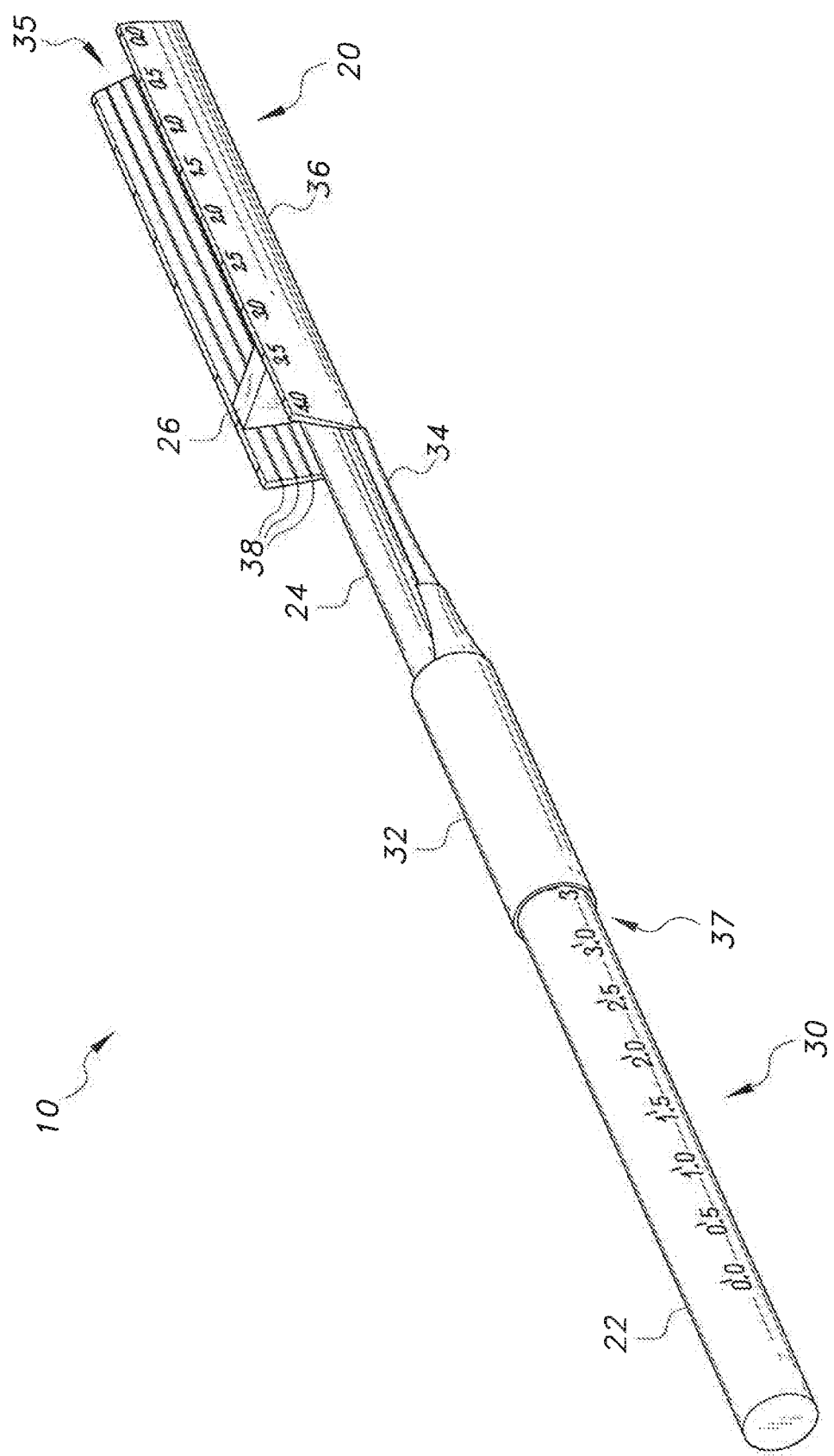
FIG. 2 is a perspective view of the applicator if FIG. 1 in an assembled configuration.

FIG. 2 shows the applicator 10 in an assembled configuration. The guide member 22 of the pusher 20 is positioned within the sheath 32 of the graft container 30 and the block 26 is seated within the channel 35 of the trough 36.

Figure 3:
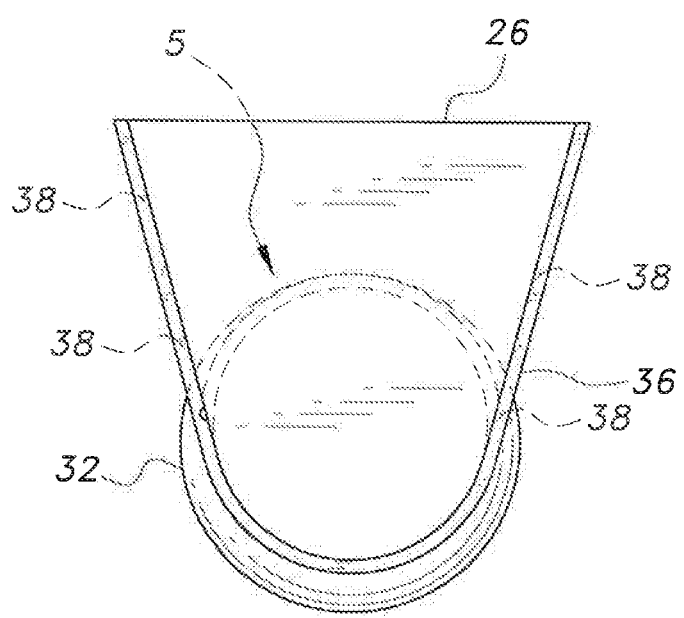
FIG. 3 is a distal view of the assembled applicator shown in FIG. 2.

FIG. 3 shows a view of the applicator 10 in an assembled position from the distal end. As previously discussed, the trough 36 and outer surface of the block 26 may be generally U-shaped. In other embodiments, the trough 36 and outer surface of the block 26 may have different shapes for procedures that benefit from grafts having specific cross-sectional shapes. The block 26 may be sized to completely fill the channel 35 defined by the trough 36 to ensure all of the semisolid material is dispensed when the trough 36 is slid past the pusher 26.

A method of using the semisolid graft applicator 10 for a rhinoplasty procedure may include first positioning the block 26 within the trough 36 based on an intended size of the graft. This step may include using the measuring scales on the trough 36 and/or guide member 22. Once the block 26 is properly positioned, the portion of the trough 36 distal to the block 26 may be filled with a semisolid mixture of diced cartilage and platelet-rich fibrin. The trough 36 may then be inserted into an opening made in the dorsum of a patient's nose until the graft is in a desired position. Once the graft is in the desired position, the pusher 20 is held in place and the graft container 30 is slid proximally until the block 26 reaches the distal end of the trough 36, thus dispensing the graft at the desired position while maintaining the shape and thickness of the graft.

It is to be understood that the semisolid graft applicator is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A semisolid graft applicator, consisting of:
   a graft container, the graft container consisting of a U-shaped trough defining a continuous open channel at the distal end of the graft container, a tubular sheath at the proximal end of the graft container, and a guide rail extending between the trough and the tubular sheath, the tubular sheath consisting of a conduit extending therethrough;
   a pusher, the pusher consisting of an imperforate distal block, a proximal cylindrical guide member, and a central elongate portion extending between the block and the cylindrical guide member, the distal block extending outwardly from the central elongate portion, wherein the proximal cylindrical guide member is sized and configured to freely slide within the tubular sheath of the graft container; further wherein the distal block is sized and configured to freely slide within the open channel; and
   a measuring scale provided on an outer surface of the trough, the trough measuring scale comprising a plurality of markers evenly spaced apart along the length of the trough and indicia indicating how far each marker is from a distal end of the trough and a measuring scale provided on an outer surface of the guide member, the guide member measuring scale comprising multiple markers evenly spaced apart along a length of the guide member and notations indicating how far a distal end of the pusher is from a distal end of the trough.

* * * * *